(12) United States Patent
Ding et al.

(10) Patent No.: US 8,655,048 B2
(45) Date of Patent: Feb. 18, 2014

(54) APPARATUS AND METHOD FOR MEASURING SIZE DISTRIBUTION OF GRANULAR MATTER

(75) Inventors: Feng Ding, Québec (CA); Richard Gagnon, Québec (CA); Claude Lejeune, Québec (CA)

(73) Assignee: Centre de Recherche industrielle du Quebec, Quebec (CA)

( * ) Notice: Subject to any disclaimer, the term of this patent is extended or adjusted under 35 U.S.C. 154(b) by 296 days.

(21) Appl. No.: 12/811,872

(22) PCT Filed: Feb. 5, 2009

(86) PCT No.: PCT/CA2009/000144
§ 371 (c)(1),
(2), (4) Date: Jul. 7, 2010

(87) PCT Pub. No.: WO2009/097687
PCT Pub. Date: Aug. 13, 2009

(65) Prior Publication Data
US 2010/0284609 A1    Nov. 11, 2010

(30) Foreign Application Priority Data
Feb. 5, 2008    (CA) .................................. 2619904

(51) Int. Cl.
*G06K 9/00*    (2006.01)

(52) U.S. Cl.
USPC ........................................................ 382/141

(58) Field of Classification Search
None
See application file for complete search history.

(56) References Cited

U.S. PATENT DOCUMENTS

| | | |
|---|---|---|
| 4,806,014 A | 2/1989 | Einarson et al. |
| 5,078,274 A | 1/1992 | Brown |
| 5,298,119 A | 3/1994 | Brown |
| 5,503,712 A | 4/1996 | Brown |
| 6,122,065 A | 9/2000 | Gauthier |
| 6,606,405 B1 | 8/2003 | Nader et al. |
| 6,960,756 B1 | 11/2005 | Penumadu et al. |
| 7,084,989 B2 | 8/2006 | Johannesson et al. |
| 7,177,487 B2 | 2/2007 | Neuberger et al. |
| 7,260,244 B2 * | 8/2007 | Shikami et al. ............... 382/112 |
| 7,292,949 B2 | 11/2007 | Ding |
| 7,429,999 B2 | 9/2008 | Poulin et al. |
| 2003/0053707 A1 * | 3/2003 | Bhattacharjya ............... 382/260 |
| 2006/0055934 A1 | 3/2006 | Sunshine et al. |

OTHER PUBLICATIONS

Thurley et al., "An industrial 3D visiion system for size measurement of iron ore green pellets using morphological image segmentation", Dec. 21, 2007, Minerals Engineering, vol. 21, iss. 5, p. 405-415.*

(Continued)

*Primary Examiner* — Stephen R Koziol
*Assistant Examiner* — Timothy Choi
(74) *Attorney, Agent, or Firm* — Jean-Claude Boudreau

(57) ABSTRACT

A method and apparatus for measuring size distribution of bulk matter consisted of randomly orientated granules, such as wood chips, make use of scanning the exposed surface of the granular matter to generate three-dimensional profile image data defined with respect to a three-coordinate reference system, The image data is segmented to reveal regions associated with distinct granules, and values of the size-related parameter for the revealed regions are estimated. Then, a geometric correction to each ones of estimated size-related parameter values is applied, to compensate for the random orientation of corresponding distinct granules. Finally, the size distribution of bulk matter is statistically estimated from the corrected size-related parameter values.

12 Claims, 15 Drawing Sheets

(56) References Cited

OTHER PUBLICATIONS

Casasent et al., "Optical symbolic substituion for morphological transformations," Sep. 15, 1988, Applied Optics, vol. 27, iss. 18, p. 3806-3810.*

Hatton, Chip Quality Monograph; Chapter 14 Chip quality analytical procedures, Joint Textbook Committee of the Paper Industry—TAPPI, pp. 303-323, Atlanta, GA, 1979.

Pulli et al., Range Image Segmentation for 3-D Object Recognition, University of Pennsylvania—Department of Computer and Information Science, Technical Report No. MS-CIS-88-32, 156p., 1988.

Chavez et al. Sampling problems during grain size distribution measurements. Proceedings or the Fifth Internatioonal Symposium on Rock Frangmentation by Blasting, Montreal, Quebec, Canada, Mohanty (ed.) 1996, pp. 245-252.

* cited by examiner

APPARATUS AND METHOD FOR MEASURING SIZE DISTRIBUTION OF GRANULAR MATTER

FIELD OF THE INVENTION

The present invention relates to the field of granular matter size measurement instrumentation, and more particularly to a method and apparatus for measuring granular matter size using computer image processing.

BACKGROUND OF THE INVENTION

Many industrial processes require the use of optical-based measurement instrumentation for obtaining data regarding size distribution of granular matter in the form of particles, fragments or flakes that are to be handled in bulk during their processing, such as ore processed in mining industry, wood chips used to produce pulp and paper and mill waste matter used in the manufacturing of fibreboards. Uniform chip size is very important for the production of high quality pulp. Changes in the distribution of sizes influence chip bulk density under a dynamic feeding condition, and therefore influence the specific energy applied at the refining stage. Oversize chips require more energy and produce poor pulp quality, while fines and pin chips decrease the pulp strength. Several types of chip classifiers are available for off-line laboratory testing, and few systems have been proposed to perform on-line discontinued measurements, as discussed by Bergman, T. in "On-line Chip Analysis: New Technology for an Improved Pulping Process", *Pulp & Paper Canada*, (12) 150-151 (1999). These measurements took only one portion of the wood chips for evaluating the size distribution of all chips, and were not really representative. For example, the well known Williams classifier makes use of superposed sifting trays of decreasing perforations sizes (Typically: ⅛<size<⅜ in.; ⅜<size<⅝ in.; ⅝<size<⅞ in.; ⅞<size<1⅛ in.; size>1⅛ in.) to physically separate the wood chips of a test sample according to increasing grain sizes, thus producing a plurality of sub-samples that are subsequently weighted to obtain a weight distribution in function of grain size classes. Chip size classification using a chip classifier such as Williams is frequently performed at chip reception sites of mills, but this offline measurement cannot be conveniently used to stabilize and control a TMP process. In order to perform an on-line chip size distribution measurement, a computerized grain size measurement method using image processing technique is preferably used, such as disclosed in U.S. Pat. No. 7,292,949 issued to the same assignee as of the present patent application. The process of computing grain size is similar to sifting sand through a screen. By gradually increasing the screen size, only the larger sand grains will be left at the end of the sifting process. As a result, the number and weight of sand grains can be plotted as a function of screen size. The resulting curve represents the grain size distribution of the particles in the tested sample. While such on-line computerized grain size measurement technique presents advantages compared with off-line Williams classifier, its accuracy has proved to be limited.

SUMMARY OF THE INVENTION

It is an object of the present invention to provide a method and apparatus for measuring size distribution of granular matter, which are capable of compensating for the random orientation of the granules constituting such matter.

According to a first broad aspect of the invention, there is provided a method for measuring size distribution of bulk matter consisted of randomly orientated granules, comprising the steps of: i) scanning an exposed surface of the granular bulk matter to generate three-dimensional profile image data defined with respect to a three-coordinate reference system; ii) segmenting the image data to only reveal regions of said image data having edges associated with distinct ones of said granules which are visible substantially without overlap; iii) estimating values of at least one size-related parameter for the revealed regions of the segmented image data; iv) applying a geometric correction to each one of said estimated size-related parameter values to compensate for the random orientation of the corresponding distinct granules; and v) statistically estimating the size distribution of bulk matter from the corrected size-related parameter values.

According to a second broad aspect of the invention, there is provided an apparatus for measuring size distribution of bulk matter consisted of randomly orientated granules, comprising means for scanning an exposed surface of the granular bulk matter to generate three-dimensional profile image data defined with respect to a three-coordinate reference system, and data processing means for segmenting the image data to only reveal regions of the image data having edges associated with distinct ones of said granules which are visible substantially without overlap, for estimating values of at least one size-related parameter for the revealed regions of segmented image data, for applying a geometric correction to each one of said estimated size-related parameter values to compensate for the random orientation of the corresponding distinct granules, and for statistically estimating the size distribution of bulk matter from the corrected size-related parameter values.

BRIEF DESCRIPTION OF THE DRAWINGS

Exemplary embodiments of the proposed system and method for measuring granular matter size will be described below in view of the accompanying drawings in which.

DETAILED DESCRIPTION OF THE EMBODIMENTS

Figure 1:
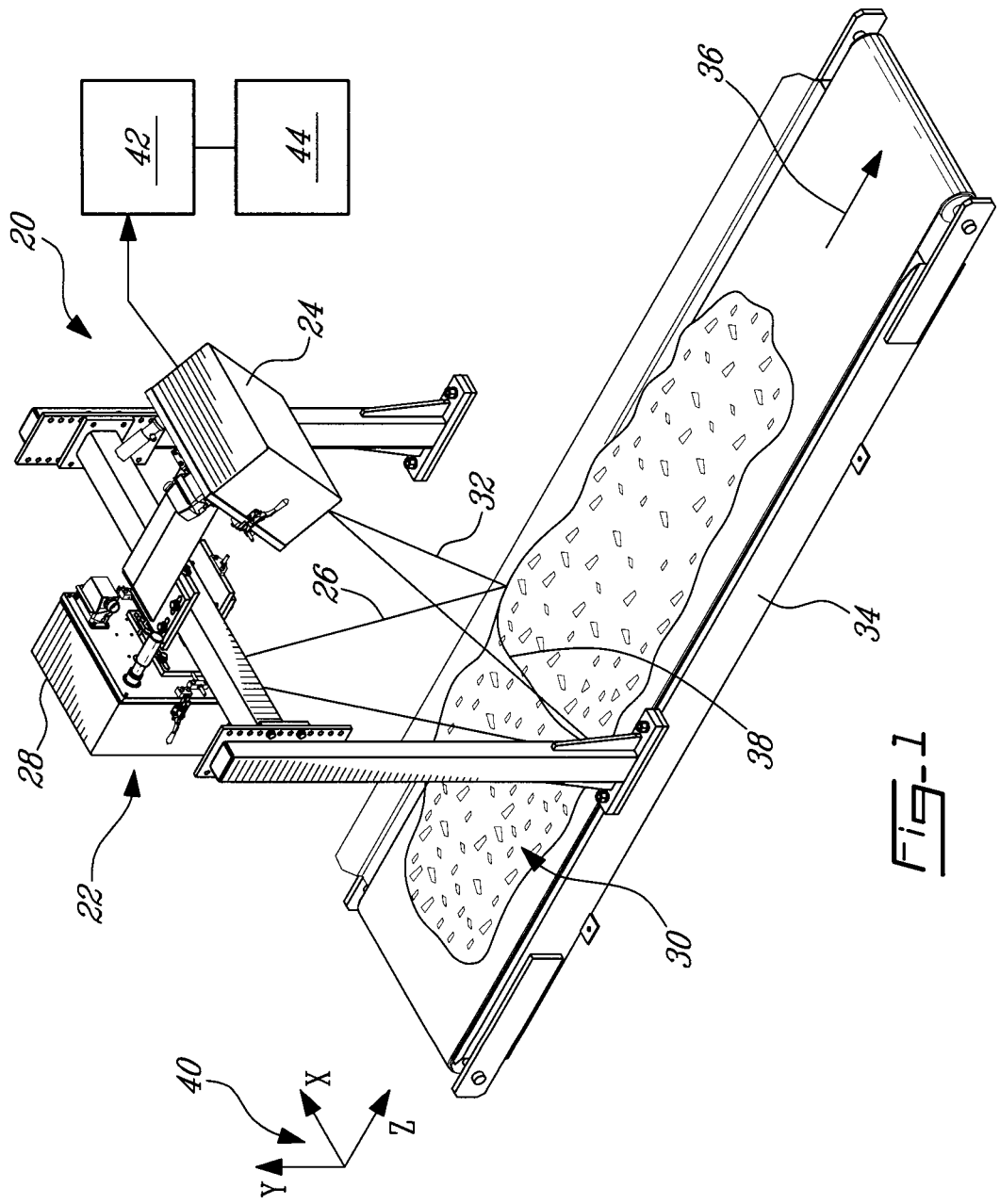
FIG. 1 is a perspective view of a granular matter size measuring apparatus according to an exemplary embodiment.
Figure 2:
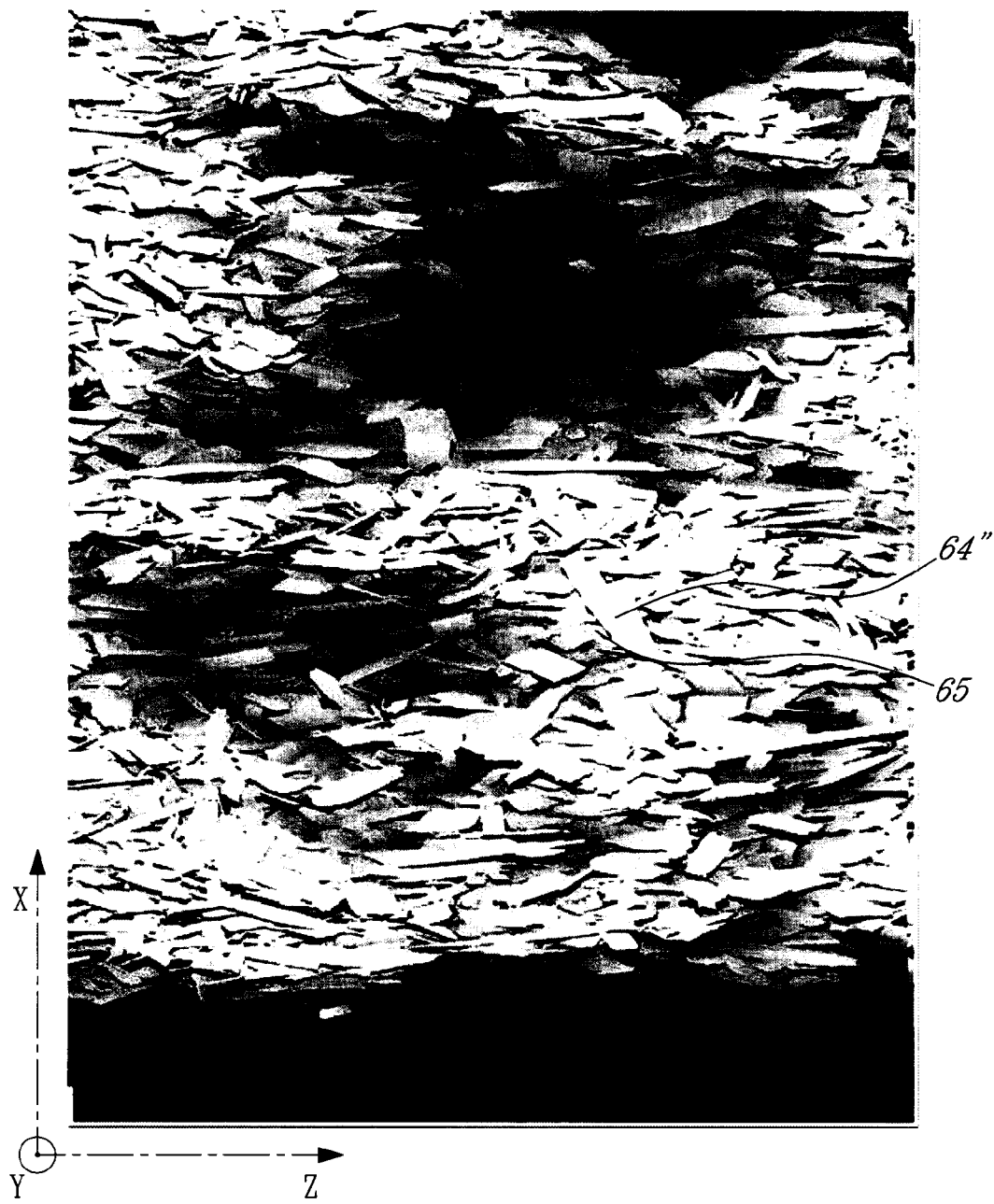
FIG. 2 is an example of raw 3D image obtained with the granular matter size measuring apparatus of FIG. 1.
Figure 3:
FIG. 3 is a conventional 3D representation of an image such as shown in FIG. 2.

The proposed granular matter size measuring apparatus and associated measuring method use a three-dimensional (3D) imaging principle. Referring to FIG. 1, the apparatus 20 according to the shown embodiment includes a profile scanning unit 22 using a matrix camera 24 for capturing an image of a linear beam 26 projected by a laser source 28 onto the granular matter 30 moving under the field of vision 32 of camera 24, the matter 30 being transported on a conveyor 34 in the direction of arrow 36 in the example shown, which field of vision 32 forming a predetermined angle with respect to the plane defined by the laser beam 26. A linear array of pin-point laser sources could replace the linear laser source, and laser scanning of the surface of a still mass of granular matter could also be used. Since all points of the laser line 38 formed on the surface of matter 30 lay in a same plane, the height of each point of line 38 is derived through triangulation computing by the use of a pre-calculated look-up table, so to obtain the X and Y coordinates of the points on the surface of the inspected matter, in view of the three-coordinate (3D) reference system designated at 40. The triangulation may be calibrated with any appropriate method, such as the one described in U.S. Pat. No. 7,429,999 issued to the same assignee as the present application. Alternatively, such as described in Canadian patent no. CA 2,237,640 also issued to the same assignee, a camera with a field of vision being perpendicular to the X-Y plane could be used along with a laser source disposed at angle, upon adaptation of the triangulation method accordingly. The triangulation program can be integrated in the built-in data processor of camera 24 or integrated in the data processor of computer 42 provided on the apparatus 20, which computer 42 performs acquisition of raw image data and processing thereof in a manner described below, the images being displayed on monitor 44. The third dimension in Z is given by successive images generated by camera 24 due to relative movement of matter 30. Hence, a 3D image exempt from information related to the coloration of inspected granular matter is obtained, such as the raw image shown in FIG. 2, wherein the grey levels of the points in the image do not represent the actual hue of the imaged surface, but rather provide a height indication (e.g. clearer is the hue, higher is the point). FIG. 3 shows a conventional 3D representation of a raw image such as shown in FIG. 2.

Figure 4:
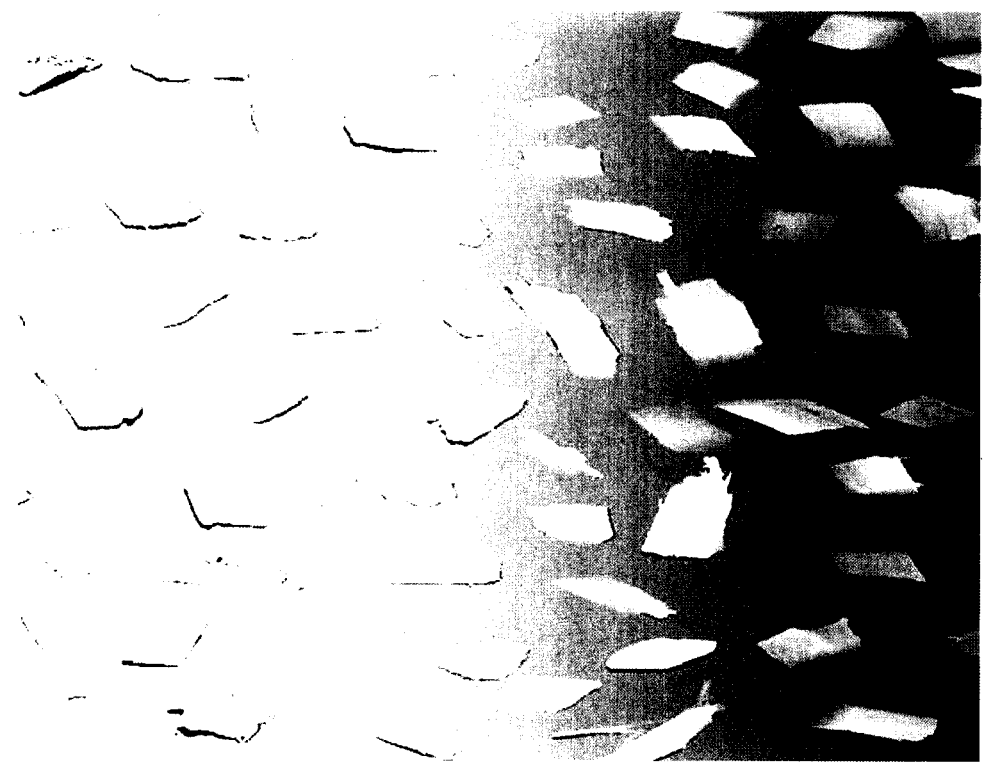
FIG. 4 represents a view of a wood chip sample spread on the surface of a conveyer for estimating the actual distributions of areas.
Figure 5:
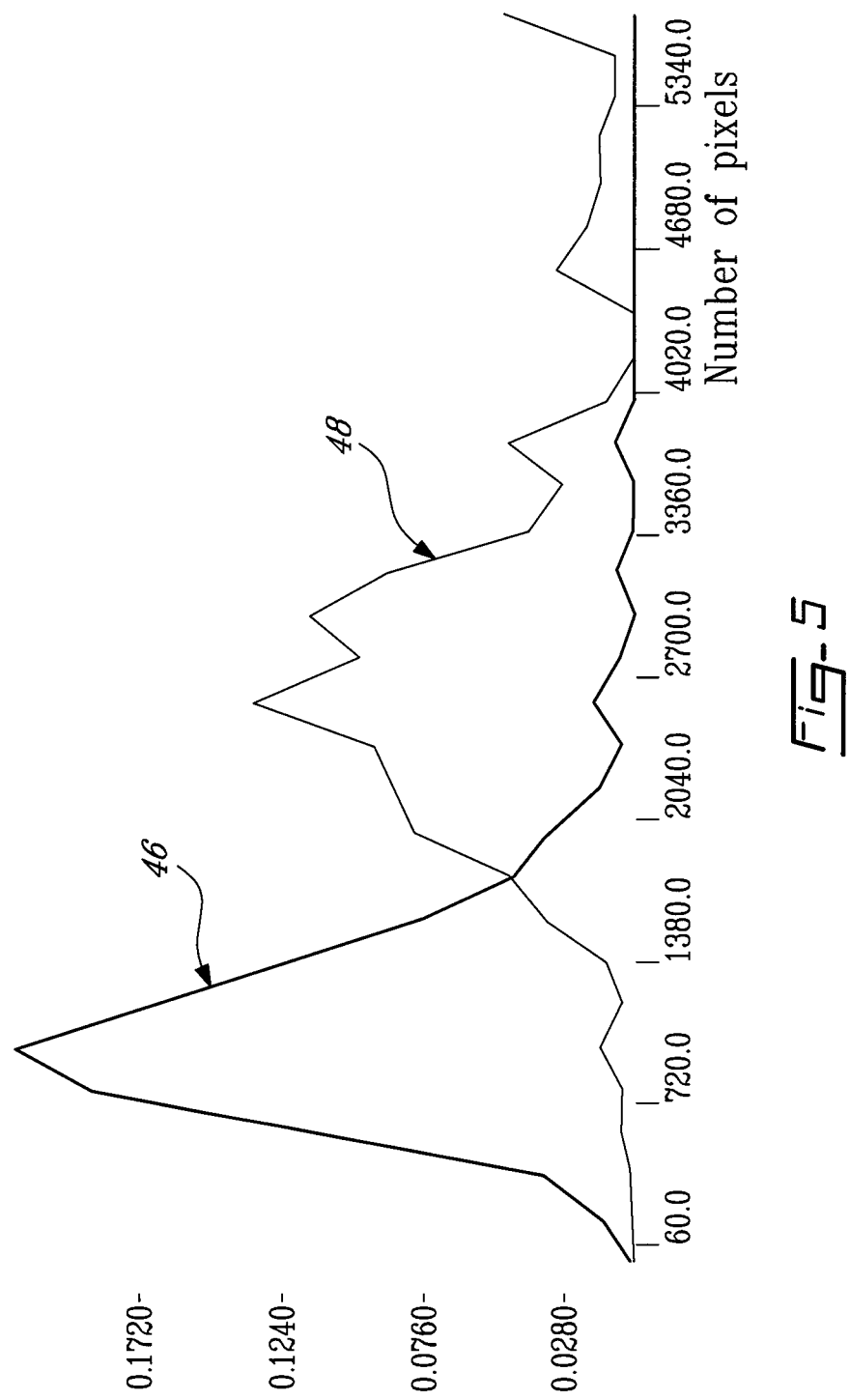
FIG. 5 is a graph presenting the curves of actual distributions of the areas of spread wood chips obtained from the batches sifted to 9.5 mm (⅜ in) and 22 mm (⅞ in)

According to the proposed approach, there is a one-to-one relation between the distribution of size-related parameter values as measured on bulk matter through 3D image segmentation processing, and the actual distribution determined from the analysis of individual granules. That relation was confirmed experimentally from a sample of wood chips (few hundreds of liters) that was sifted to produce five (5) batches of chips presenting distinct size characteristics such as expressed by statistical area distributions. The actual distributions of chip areas were measured by spreading the chips on the conveyer in such a manner that they can be isolated as shown in FIG. 4. Ten (10) images for each chip batch enabled obtaining reliable statistical data associated with a sample of about two thousand (2000) chips. Since sifting separates chips according to a single dimension, a Gaussian (normal) area distribution was observed for each sifted batch, such as exhibited by curves 46 and 48 on the graph of FIG. 5, for the batches sifted to 9.5 mm (⅜ in) and 22 mm (⅞ in), respectively. Although the following section describes size measuring methods in the context of an application for granular matter constituted of wood chips to produce pulp and paper, it is to be understood that, provided said one-to-one relation between the distribution of size-related parameter values as measured and the actual distribution exists, these methods are also intended for application to granular matter of other nature, in the form of particles, fragments or flakes that are to be handled in bulk during their processing, such as ore processed in mining industry, and mill waste matter used in the manufacturing of fibreboards.

A good segmentation algorithm exhibits an optimal trade-off between the capability of detecting with acceptable certainty a wholly visible chip substantially without overlap, and the capability of isolating a maximum number of chips in a same image so that the required statistical data could be acquired in a sufficiently short period of time. Many 3D image segmentation methods have been the subject of technical publications, such as those described by Gupta in <<Range Image Segmentation for 3-D Object Recognition>> University of Pennsylvania—Department of Computer and Information Science, Technical Report No. MS-CIS-88-32, May 1988, and by Gachter in <<Results on Range Image Segmentation for Service Robots>> Technical Report, Ecole Polytechnique Fédérale de Lausanne—Laboratoire de Système Autonomes, Version 2.1.1, September 2005.

Figure 6:
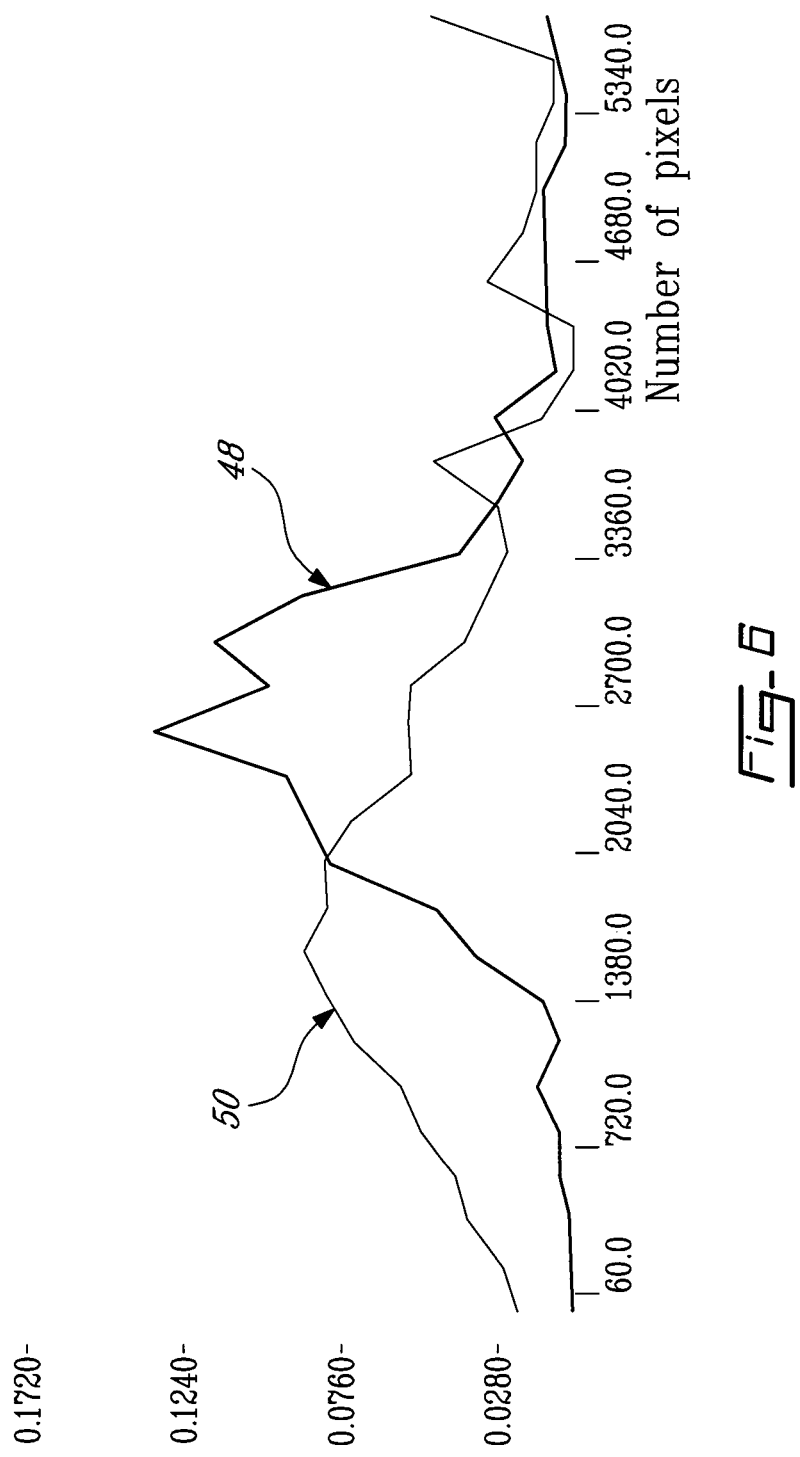
FIG. 6 is a graph presenting the curve of actual distribution of the areas of spread wood chips obtained from the batch sifted to 22 mm (⅞ in), and the curve of distribution estimated from a segmentation of 3D images of the same wood chips as inspected in bulk.
Figure 7:
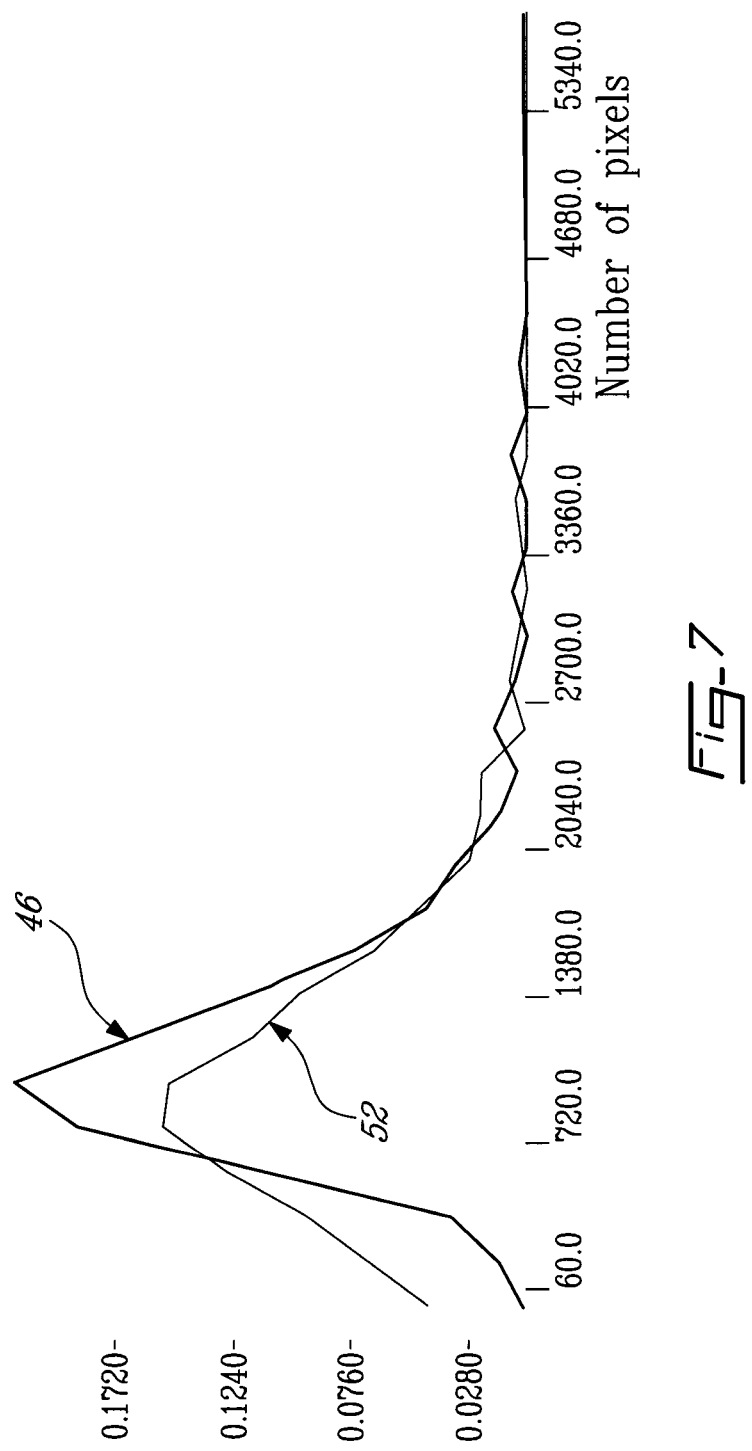
FIG. 7 is a graph presenting the curve of actual distribution of the areas of spread wood chips obtained from the batch sifted to 9.5 mm (⅜ in), and the curve of distribution estimated from a segmentation of 3D images of the same chips as inspected in bulk.

The graph of FIG. 6 presents a curve 48 of actual distributions for spread chips and a curve 50 of distributions estimated from 3D image segmentation for chips from the batch sifted to 22 mm (⅞ in), using a basic segmentation method carried on by a program coded in C++ and executed by computer 42. The graph of FIG. 7 presents a curve 46 of actual distributions for spread chips and a curve 52 of distributions estimated from 3D image segmentation for chips from the batch sifted to 9.5 mm (⅜ in). It can be observed from these graphs that estimations obtained with segmentation also provide a Gaussian distribution, but with a mean shifted toward the lowest values and with a higher spread (variance). Such bias can be explained by the fact that granules in bulk are found in random orientations thus generally reducing the estimated area for each granule on the one hand, and by the fact that the segmentation algorithm used, although appropriate, would have a tendency to over-segmentation, on the other hand, thus favouring the low values. Notwithstanding that bias, at least for a Gaussian distribution, it is clear that a one-to-one relation exists between the distributions measured on chips in bulk and those of spread chips, whenever any appropriate segmentation method is used.

Figure 8:
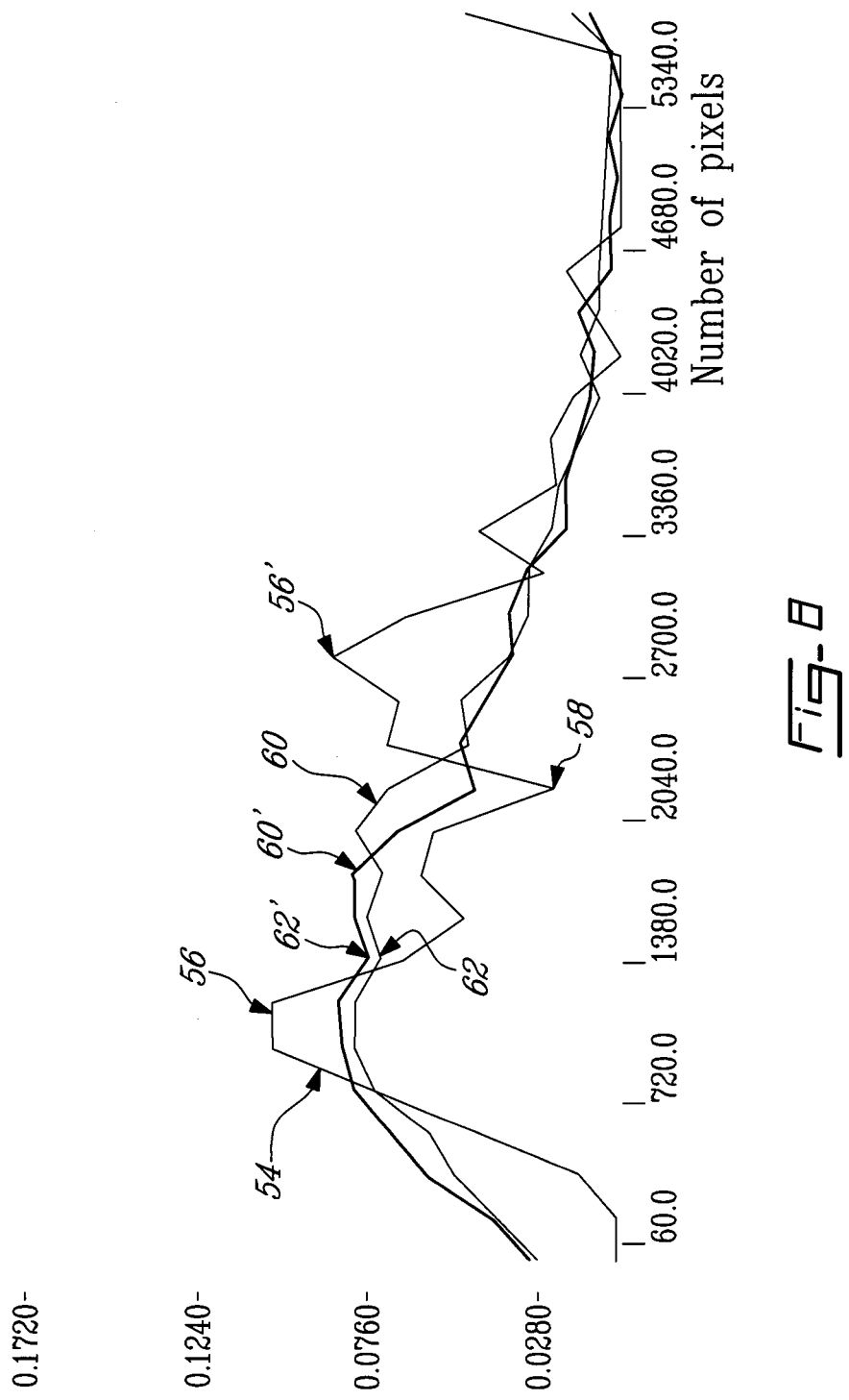
FIG. 8 is a graph presenting the curve of actual distribution of the areas of spread wood chips obtained from a mix of chips from the batches sifted to 9.5 mm (⅜ in) and 22 mm (⅞ in), and the curves of distributions of areas of the same chips as inspected in bulk following the segmentation of a set of images.

A chip sample characterized by a non-Gaussian distribution was produced by mixing chips from batches sifted to 9.5 mm (⅜ in) and 22 mm (⅞ in). The graph of FIG. 8 shows a curve 54 of distribution of areas obtained with spread chips. That distribution exhibits two (2) peaks 56 and 56' separated by a local minimum 58 associated with absence of chips from the 16 mm (⅝ in) group. Curves 60 and 60' of the same graph show the estimated distributions of areas following segmentation of sets of ten (10) and twenty (20) images of chips in bulk, respectively. Here again, one can observe a shift of means and a spread of peaks causing an overlap of the Gaussian distributions associated with the two batches of chips. Nevertheless, the presence of inflection points 62,62' located near the apex of the distributions of curves 60, 60' indicates that two batches are involved, whose individual means can be estimated.

The experiences that were performed have demonstrated the reliability of estimation of area distribution for chips in bulk using 3D image analysis of chip surface. The estimations were found sufficiently accurate to produce chip size data usable for the control of a pulp production process. That conclusion is valid provided that the exposed chips located on top of an inspected pile of chips are substantially representative thereof as a whole, and that the segmentation-induced bias is substantially constant. In cases where some segregation of granules occurs on the transport line, a device forcing homogenization can be used upstream the measuring apparatus 20. Moreover, to the extent the batches of granules are produced through identical or equivalent processes, one can assume that the granule characteristics influencing the segmentation bias are substantially constant. Nevertheless, in the case of wood chips, since it is possible that their forms vary somewhat with species, temperature at the production site and cutting tool wear, these factors may limit the final estimation accuracy. The spread of Gaussian distributions and the bias toward low values of mean area measurements can be reduced through geometric corrections applied to area calculations, which corrections, conveniently calculated with a 3D regression plane, consider the orientation of each segmented granule, as described below.

In the following sections, a more detailed description of image processing and analyzing steps is presented.

Figure 9:
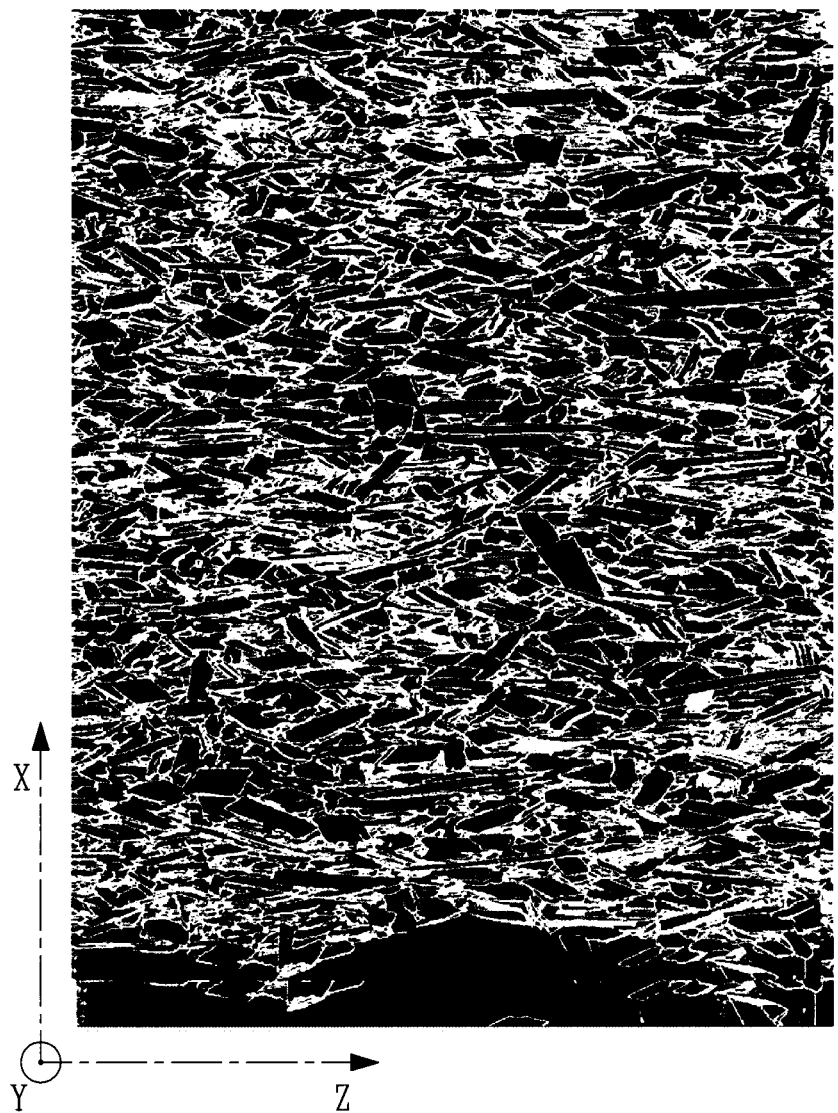
FIG. 9 is an example of 3D image processed with the application of a gradient during the segmentation step.

The segmentation step aims at revealing regions of image data represented by groups of pixels associated with distinct granules. In the example involving wood chips, starting with a 3D image such as shown in FIG. 2, a second image is generated by taking the absolute value of maximal gradient calculated on a pixel-by-pixel basis, conveniently considering the eight (8) nearer neighbouring pixels. The calculated values are limited to a predetermined maximal value, to obtain gradient-processed image data such as represented in FIG. 9, wherein high intensity pixels reveal edges associated with either distinct granules or portions thereof.

Figure 10:
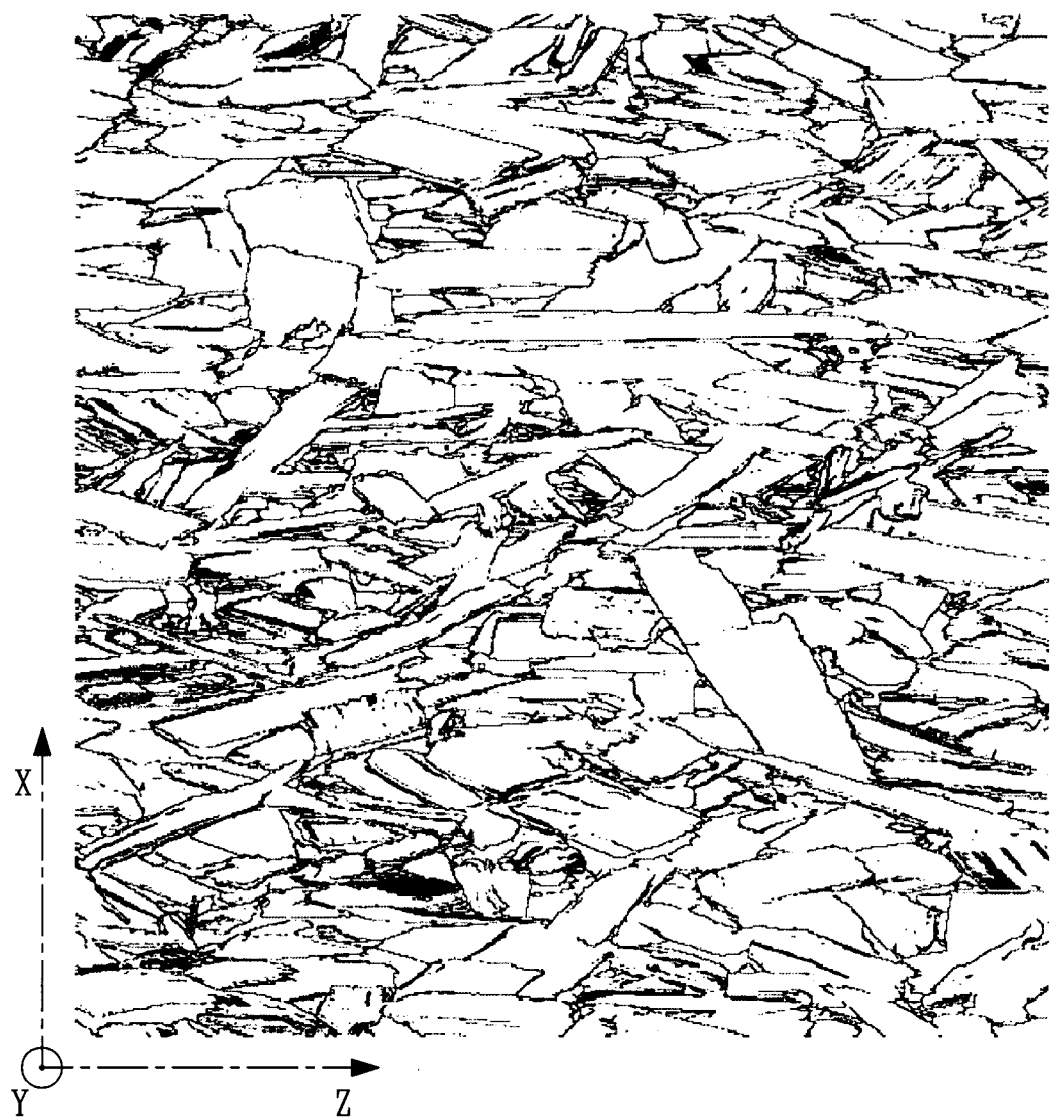
FIG. 10 is a portion of an inverted binary image obtained with thresholding from the image of FIG. 9.

Then, a thresholding is performed to generate binary image data, conveniently in an inverted imaging mode, such as represented by the image portion shown in FIG. 10. The thresholding parameters are set in such a manner to retain a sufficient number of significant pixels necessary for the following processing steps.

Figure 11:
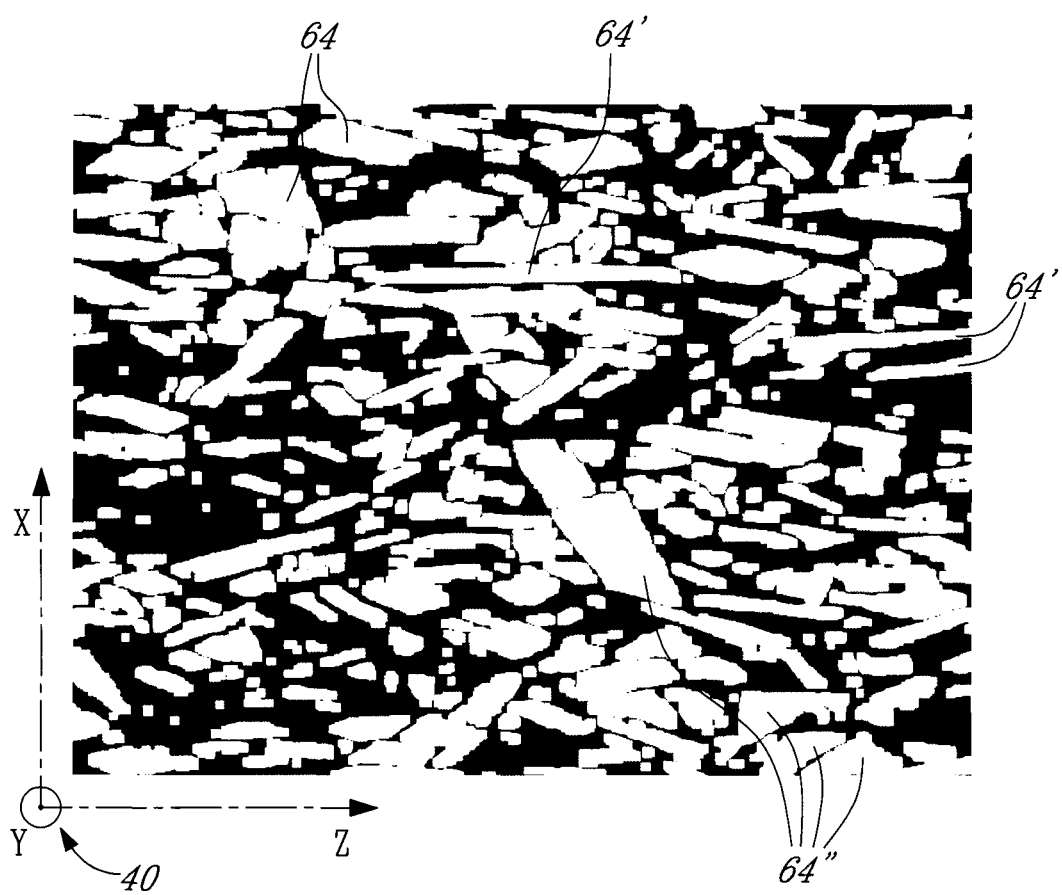
FIG. 11 is a portion of an image obtained with morphological operations of dilatation and erosion from the image portion of FIG. 10.

Morphological operations of dilatation and erosion are followed to eliminate or at least reduce noise, to bind isolated pixels surrounding any revealed regions of image data, and to promote contour closing of revealed regions, providing an image such as shown in FIG. 11. These morphological operations can be implemented through custom software programmed by any person skilled in the art of computer programming, or be performed with software tools available on the marketplace such as the Matrox Imaging Library (MIL 9.0) from Matrox (Montreal, Canada), or with any other appropriate software tool for morphologic processing such as provided in Open Computer Vision Library (OpenCV) as readily available in open source through the Internet under a Berkely Software Distribution (BSD) Licence.

The contour of each region 64 found in a partially processed image such as shown in FIG. 11 delimits an area with respect to a two-coordinate subsystem defined by axes X and Z included in three-coordinate reference system 40 referred to above in view of FIG. 1. From the contours, a preliminary selection of regions to retain for statistical calculations that will be described below is performed by eliminating the regions of image data whose contour perimeter is too long with respect to area to belong to a single granule (multi-granule regions). For so doing, any appropriate blob analysis software tool such as provided in the Matrox Imaging Library or in OpenCV may be used. Any region whose ratio of contour to area is higher than a first predetermined maximum value is excluded from the revealed regions, such as performed on the resulting image shown in FIG. 12, wherein it can be seen by comparison with the preceding image of FIG. 11 that regions 64' have been excluded, while regions 64" have been retained. Since the random orientation of granules in bulk statistically causes some overrepresentation of small regions as compared to large regions in an image under processing, different maximum values may be applied depending on region's area to compensate for such bias. For example, a "high" maximum value may be used in cases where granule's area is under a preset limit in order to apply a strict selection test to small regions, while a "low" maximum value may be used whenever region's area fall over the preset limit, to apply a less stringent selection test in favour or large regions.

Figure 12:
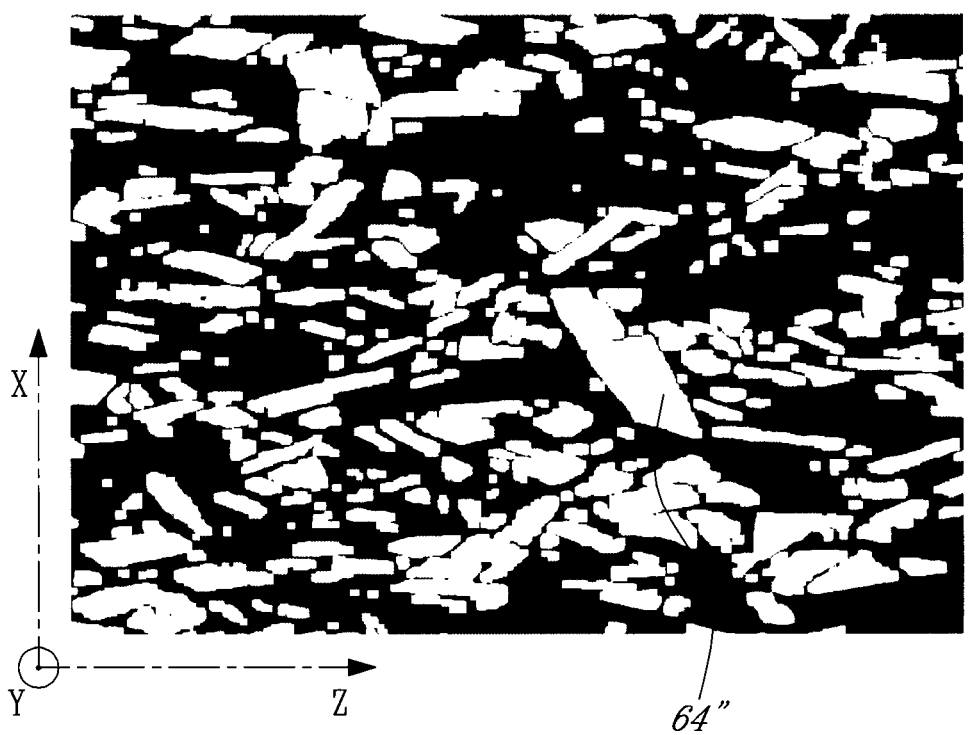
FIG. 12 is a portion of an image obtained through a preselection according to a contour perimeter/area ratio for regions within the image portion of FIG. 11 to retain for generating statistical data.
Figure 13:
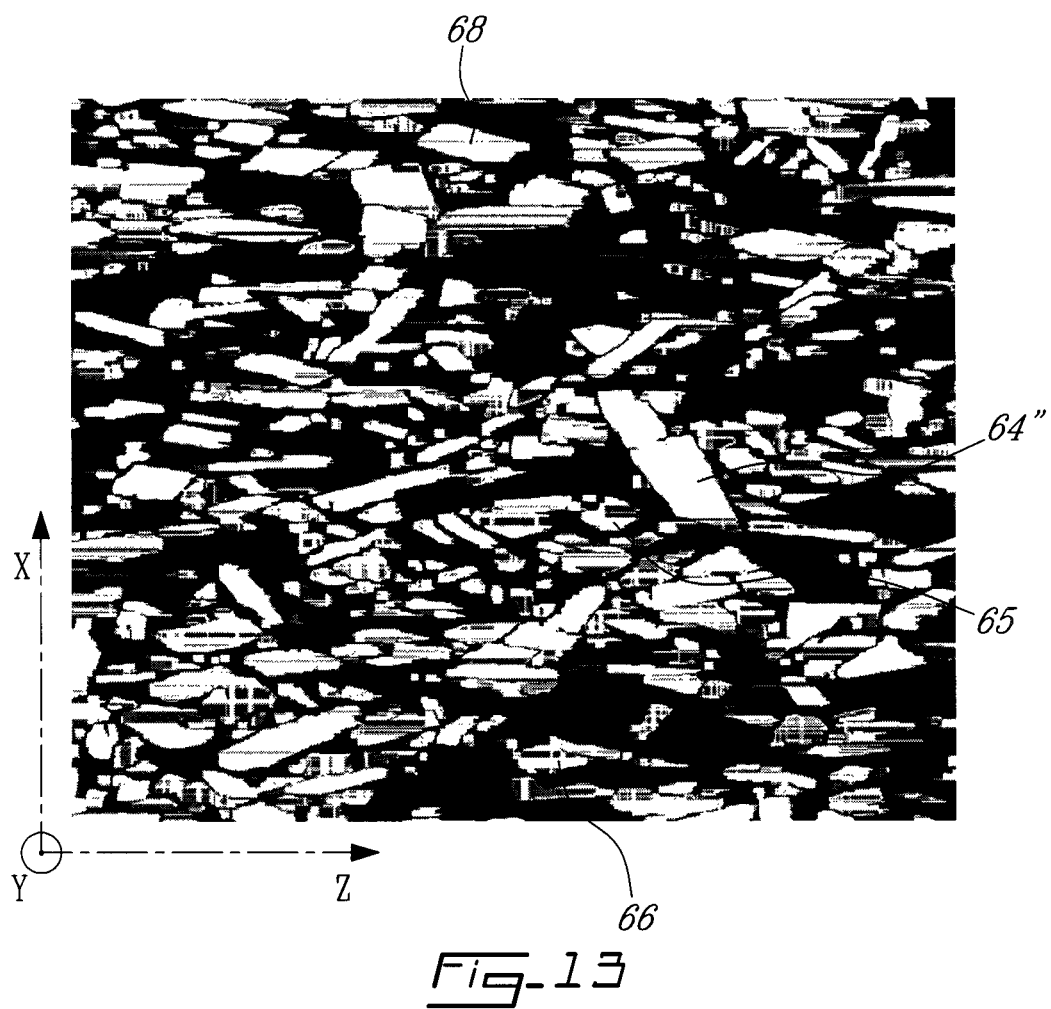
FIG. 13 is a portion of an image produced by filtering of the image portion of FIG. 16 for locating obstruction zones.

Then, remaining obstructed portions of regions resulting from overlapping granules are searched and located by appropriate image filtering. A way to achieve that goal consists of applying a step filter according to lines and columns of the preceding image such as shown in FIG. 12. Hence, a processed image such as shown in FIG. 13 is obtained, wherein the columns such as 66 and lines such as 68 where an obstruction has been detected are indicated by distinct levels of grey (e.g. columns: pale, lines: dark). Then, any region whose ratio of obstructed area portion to unobstructed area portion (in percentage of area) is higher than a second predetermined maximum value is excluded from the revealed regions. For so doing, the computer program may implement a selection function that is dependent upon the obstruction ratio. That function enables the selection of groups of pixels associated with image regions corresponding to distinct granules, by retaining the granules characterized by a slight obstruction while eliminating the granules having a major hidden portion. According to a similar approach as applied for the purpose of the preliminary selection as described above, due to the random orientation of granules in bulk, different maximum values for the obstruction ratio may be applied depending on region's area to compensate for the bias.

Figure 14:
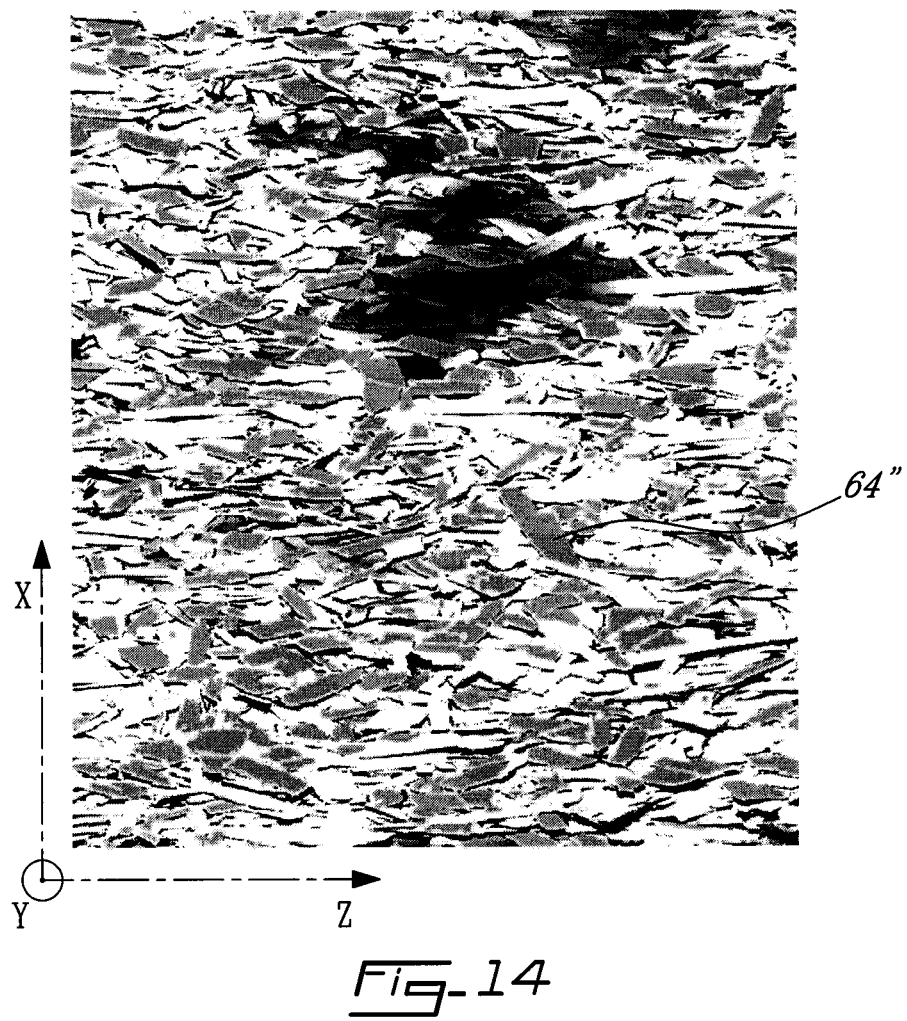
FIG. 14 is a final image resulting from the segmentation step, superimposed on the raw image of FIG. 2.

FIG. 14 is an example of final image resulting from the segmentation step, superimposed on the raw image of FIG. 2 and showing the distinct particles such as 64" in grey. It can be seen that the region designated at 65 on FIGS. 2 and 13 has been excluded from the revealed regions through the segmentation step resulting in the final image shown in FIG. 14, while region 64" has been retained.

Figure 15:
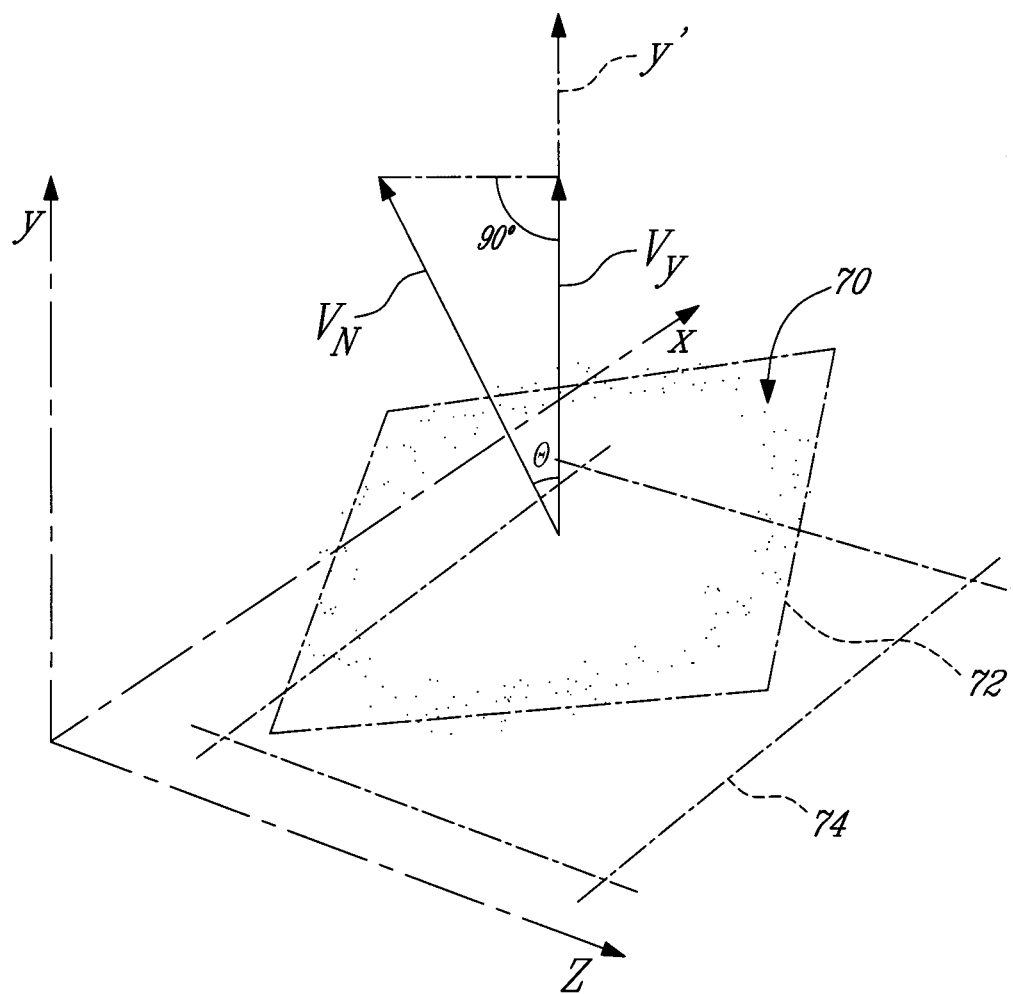
FIG. 15 is a graph representing an example of a region of image data associated with a granule, showing a plane defined for the purpose of calculating a geometric correction to compensate for the random orientation of the granule.

As mentioned above, the last step before statistical data compiling consists of computing the geometric correction to the estimated size-related parameter values to compensate for the random orientation of corresponding granules. Referring to the graph of FIG. 15, there is represented a revealed region of image data generally designated at 70 and being associated with a distinct granule for which the desired size-related parameter is to be measured with appropriate geometric correction. For that purpose, a plane 72 represented by truncated lines as passing substantially through the exposed surface of revealed region 70 is defined. Conveniently, a surface-fitting algorithm such as multi-variable regression is applied to the revealed region of image data to determine the spatial characteristics of plane 72. Then, the geometric correction can be derived from an angular relationship between the plane 72 and a reference plane 74 also represented by truncated lines in FIG. 15, which plane 74 is defined by the three-coordinate reference system 40. Conveniently, the reference plane 74 is parallel to a plane defined by a two-dimensional reference subsystem formed by first and second axes X and Z of reference system 40. The angular relationship can be defined by an angle $\theta$ formed by a first vector $V_N$ normal to the plane 72, and a second vector $V_Y$ normal to the reference plane 74, which second vector $V_Y$, being parallel to third axis Y of reference system 40, is obtained through a geometrical projection at 90° against a translated axis Y' also shown in FIG. 15. The correction for the estimated size related parameter, which is surface area in the context of the present example, can be obtained using the arithmetic inverse cosine of the angle $\theta$ between first vector $V_N$ and second vector $V_Y$, according to the following relation:

$$C = \frac{1}{\cos\theta} \tag{1}$$

Hence, the corrected size-related parameter values can be derived using the following relation:

$$S_C = CS \tag{2}$$

wherein S represents each one of estimated size-related parameter values. In the context of another application, other type of size-related parameter such as length, width and diameter, could be subjected to a similar correction.

Finally, the size distribution of bulk matter is estimated from the corrected size-related parameter values, using known statistical data compiling operations. As mentioned above, the distributions observed from the inspection of granules in bulk may involve bias of a statistical nature. To the extent that the bias function is stationary, compensation thereof is possible to estimate the actual distribution from the observed one. An empirical relation linking a size distribution observed from the inspection of granules in bulk and the actual size distribution of granules constituting the inspected matter can be obtained through a determination of a square matrix of N×N elements, wherein N is the number of groups used for the distribution. By considering that each group j of the actual distribution contributes according to an amplitude $a_{ij}$ to the group i of the estimated distribution, the following relation is obtained:

$$T_i = \sum_j a_{ij} D_j \tag{3}$$

wherein $T_i$ is a normalized value of estimated distribution for a group i, and $D_j$ is the $j^{th}$ normalized value of the actual distribution. For the whole distribution, the following matrix equation is obtained:

$$T = AD \tag{4}$$

wherein T and D are column-vectors containing the observed-in bulk and actual distributions, respectively, and A is the matrix to be determined. In order to conveniently reduce from $N^2$ to 2N the number of independent parameters involved in the calculation of amplitude values $a_{ij}$, it can be assumed that the column of matrix A corresponds to the values of a Gaussian distribution according to the following relation:

$$a_{ji} = A_j e^{\frac{-(i-\mu_j)^2}{2\sigma_j^2}} \tag{5}$$

wherein:
$A_j$ is a normalisation factor;
$\mu_j$ is the Gaussian mean;
$\sigma_j$ is the Gaussian variance.

In order to reduce the number of degrees of freedom, it can be further assumed that all $\mu_j$ form an increasing monotonic sequence, while all $\sigma_j$ form a monotonic sequence that could be either increasing or decreasing. Hence, the values of $\mu_j$ and $\sigma_j$ can be estimated using the following polynomial equations of the second degree:

$$\mu_j = b_2 j^2 + b_1 j + b_0 \tag{6}$$

$$\sigma_j = c_2 j^2 + c_1 j + c_0 \tag{7}$$

wherein $b_0$, $b_1$, $b_2$, $c_0$, $c_1$, $c_2$ are coefficients that can conveniently estimated through minimization of the following error function:

$$E = |T_{inf} - T_{ref}| = \left(\sum_{j=1}^{n}(d_i - p_i)^2\right)^{\frac{1}{2}} \tag{8}$$

wherein:
$T_{inf} = AD = (p_1, p_2, \ldots, p_n)$ is an inferred size distribution obtained from the actual distribution D;
$T_{ref} = (d_1, d_2, \ldots, d_n)$ is a reference size distribution as observed from granules in bulk.

Hence, values of coefficients $b_0$, $b_1$, $b_2$, $c_0$, $c_1$, $c_2$ which minimize the error function (8) may be found by a known iterative optimization technique such as Levenberg-Marquardt or steepest descent method. Finally, one obtains an estimated size distribution as follows:

$$D_{est} = A^{-1} T \tag{9}$$

Hence, the inversion of matrix A enables to obtain the relation between any size distribution estimated from inspection of granules in bulk and the actual size distribution. It is to be understood that any other appropriate method for deriving that relation can be used, such as a method using a log-normal model rather that a Gaussian model.

We claim:

1. A method for measuring size distribution of bulk matter consisted of randomly orientated granules, comprising the steps of:
  i) scanning an exposed surface of said granular bulk matter to generate three-dimensional profile image data defined with respect to a three-coordinate reference system;
  ii) segmenting said image data to only reveal regions of said image data having edges associated with distinct ones of said granules which are visible substantially without overlap;

iii) estimating values of at least one size-related parameter for said revealed regions of segmented image data;
iv) applying a geometric correction to each said estimated size-related parameter values to compensate for the random orientation of corresponding said distinct granules; and
v) statistically estimating the size distribution of bulk matter from said corrected size-related parameter values.

2. A method according to claim 1, wherein said step ii) includes the steps of:
a) calculating an absolute value of maximal gradient of said image data on a pixel-by-pixel basis to obtain gradient-processed image data;
b) thresholding said gradient-processed image data to obtain binary image data; and
c) morphologically processing said binary image data through dilatation and erosion to reduce noise, to bind isolated pixels surrounding any said regions and to promote contour closing of said regions.

3. A method according to claim 2, wherein the contour of each said regions delimits an area with respect to a two-coordinate subsystem included in said three-coordinate reference system, said step ii) further including the step of:
d) excluding from said revealed regions any region whose ratio of contour perimeter to area is higher than a first predetermined maximum value over which the region is likely to belong to more than a distinct one of said granule.

4. A method according to claim 3, wherein said step ii) further includes the steps of:
e) filtering each said regions to locate any obstructed portion within said area; and
f) excluding from said revealed regions any region whose ratio of obstructed area portion to unobstructed area portion is higher than a second predetermined maximum value.

5. A method according to claim 1, wherein said step iv) includes the steps of:
a) defining a single plane passing substantially through the whole exposed surface of each said revealed region associated with a distinct one of said granules; and
b) deriving said geometric correction from an angular relationship between said plane and a reference plane defined by said three-coordinate reference system.

6. A method according to claim 5, wherein said single plane is defined using a surface fitting algorithm applied to said revealed region of image data.

7. A method according to claim 6, wherein said surface fitting algorithm is a multi-variable regression algorithm.

8. A method according to claim 5, wherein said reference plane is parallel to a plane defined by a two-dimensional reference subsystem formed by first and second axes and being included in said reference system, said angular relationship being defined by an angle formed by a first vector normal to said single plane and a second vector normal to said reference plane, said second vector being parallel to a third axis included in said reference system.

9. A method according to claim 8, wherein said geometric correction is derived using the following relation:

$$C = \frac{1}{\cos\theta}$$

wherein $\theta$ represents said angle.

10. A method according to claim 9, wherein said corrected size-related parameter values are derived using the following relation:

$$S_C = CS$$

wherein S represents each said estimated size-related parameter values.

11. A method according to claim 10, wherein said size-related parameter is surface area.

12. An apparatus for measuring size distribution of bulk matter consisted of randomly orientated granules, comprising:
means for scanning an exposed surface of said granular bulk matter to generate three-dimensional profile image data defined with respect to a three-coordinate reference system; and
data processing means for segmenting said image data to only reveal regions of said image data having edges associated with distinct ones of said granules which are visible substantially without overlap, for estimating values of at least one size-related parameter for said revealed regions of segmented image data, for applying a geometric correction to each said estimated size-related parameter values to compensate for the random orientation of corresponding said distinct granules, and for statistically estimating the size distribution of bulk matter from said corrected size-related parameter values.

* * * * *